US010098660B2

(12) United States Patent
Park et al.

(10) Patent No.: US 10,098,660 B2
(45) Date of Patent: Oct. 16, 2018

(54) TROCAR, METHOD FOR MANUFACTURING THE SAME, AND METHOD FOR CONTINUOUSLY MANUFACTURING THE SAME

(71) Applicant: KOREA INSTITUTE OF MACHINERY & MATERIALS, Daejeon (KR)

(72) Inventors: Jong-Kweon Park, Daejeon (KR); Seung Kook Ro, Daejeon (KR); Sung Cheul Lee, Daejeon (KR); Byung-Sub Kim, Daejeon (KR); Jaegu Kim, Daejeon (KR); Kornel Ehmann, Evanston, IL (US); Peidong Han, Evanston, IL (US)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 375 days.

(21) Appl. No.: 14/926,106

(22) Filed: Oct. 29, 2015

(65) Prior Publication Data

US 2017/0119431 A1 May 4, 2017

(51) Int. Cl.
*B24B 3/60* (2006.01)
*A61B 17/34* (2006.01)
*A61B 17/00* (2006.01)

(52) U.S. Cl.
CPC .......... *A61B 17/3417* (2013.01); *B24B 3/605* (2013.01); *A61B 2017/00526* (2013.01); *A61B 2017/3454* (2013.01)

(58) Field of Classification Search
CPC ................ B24B 3/605; A61B 17/3417; A61B 2017/00526; A61B 2017/3454
USPC .................................. 451/57, 58, 45, 28, 382
See application file for complete search history.

(56) References Cited

U.S. PATENT DOCUMENTS

| | | | | |
|---|---|---|---|---|
| 279,075 | A * | 6/1883 | Berry ..................... | B24B 41/06 451/397 |
| 2,525,264 | A * | 10/1950 | Milner .................... | B24B 19/16 451/213 |
| 2,802,310 | A * | 8/1957 | Chaplik .................. | B24B 19/16 451/226 |
| 2,838,883 | A * | 6/1958 | Hall ........................ | B24B 19/16 451/216 |
| 4,173,100 | A * | 11/1979 | MacBroom, Jr. ....... | B24B 41/06 269/43 |
| 5,575,708 | A * | 11/1996 | Chau ................ | A61B 17/06066 451/305 |
| 6,015,338 | A * | 1/2000 | Hong .................. | A61M 5/3286 451/298 |

* cited by examiner

*Primary Examiner* — Robert Rose
(74) *Attorney, Agent, or Firm* — Lex IP Meister, PLLC

(57) ABSTRACT

According to an exemplary embodiment of the present invention, a trocar is provided. The trocar includes: a sharp end; at least three concave cutting edges extended from the sharp end; and at least three concave cutting surfaces forming the sharp end and the at least three cutting edges.

8 Claims, 5 Drawing Sheets

(a)

(b)

(a)  (b)

(a)

(b)

(c)

(a)

(a)

TROCAR, METHOD FOR MANUFACTURING THE SAME, AND METHOD FOR CONTINUOUSLY MANUFACTURING THE SAME

BACKGROUND OF THE INVENTION (a) Field of the Invention

The present invention relates to a surgical instrument, and more particularly, it relates to a trocar that optimizes penetration force, a method for manufacturing the same, and a method for continuous manufacturing the same.

(b) Description of the Related Art

In general, a trocar is a surgical instrument having a sharp end for penetration into a human body. The trocar is the most generally-used medical device, and is used for minimally invasive or percutaneous treatment such as a biopsy or brachytherapy.

Referring to FIG. 1, performance of a trocar 1 may be measured by penetration force generated while the trocar 1 passes through tissue. In general, the penetration force of the trocar 1 is changed depending on an angle of the sharp end of the trocar 1 and a penetration angle thereof. The penetration force of the trocar 1 is determined by $\theta$, which is an internal angle of the sharp end of the trocar 1, and $\lambda$, which is an inclination angle of a cutting edge of the trocar 1 with respect to tissue. In detail, the trocar 1 can more smoothly penetrate skin tissue 2 as $\theta$ is smaller and $\lambda$ is larger. That is, the trocar 1 requires small $\theta$ and large $\lambda$.

However, the conventional trocar 1 has a straight-line type of blade and thus a small $\theta$ and a large $\lambda$ cannot be satisfied. Accordingly, the penetration force of the trocar 1 cannot be optimized.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a trocar having maximized penetration force, a method for easily manufacturing the same, and a method for continuously manufacturing the trocar to thereby maximize productivity. However, this is not restrictive, and thus the scope of the present invention is not limited thereto.

According to one aspect of the present invention, a trocar is provided. The trocar includes: a sharp end; at least three concave cutting edges extended from the sharp end; and at least three concave cutting surfaces forming the sharp end and the at least three cutting edges.

The at least three concave cutting edges may include: first and second cutting edges disposed opposite to and facing each other with reference to the sharp end; and third and fourth cutting edges disposed opposite to and facing each other between the first cutting edge and the second cutting edge, and being longer than the first and second cutting edges.

An angle formed by the first cutting edge, the sharp end, and the second cutting edge may be greater than an angle formed by the third cutting edge, the sharp end, and the fourth cutting edge.

According to another aspect of the present invention, a method for manufacturing a trocar is provided. The method includes: forming a concave first cutting surface by grinding a shaft extended in one direction; forming a concave second cutting surface by rotating the shaft by a predetermined angle with reference to an axis of the shaft and then grinding the shaft after forming the first cutting surface; forming a concave third cutting surface by rotating the shaft by an angle acquired by subtracting a predetermined angle from 180° with reference to the axis of the shaft and then grinding the shaft after forming the second cutting surface; and forming a concave fourth cutting surface by rotating the shaft by the predetermined angle with reference to the axis of the shaft and then grinding the shaft after forming the third cutting surface.

The forming the first cutting surface, the forming the second cutting surface, the forming the third cutting surface, and the forming the fourth cutting surface may include rotating the shaft in one of clockwise and counterclockwise directions.

The predetermined angle may be greater than 90° and smaller than 180°.

According to another aspect of the present invention, a method for continuously manufacturing a trocar is provided. The method includes: preparing a plurality of shafts in a direction that is perpendicular to an axis direction of each shaft; continuously forming a concave first cutting surface in each of the plurality of shafts by grinding the plurality of shafts using a wheel; continuously forming a concave second cutting surface by rotating each of the plurality of shafts by a predetermined angle with reference to an axis of each of the plurality of shafts and grinding the respective shafts using the wheel; continuously forming a concave third cutting surface by rotating the respective shafts by an angle acquired by subtracting a predetermined angle from 180° with reference to the axis of each shaft and grinding the respective shafts using the wheel; and continuously forming a concave fourth cutting surface by rotating the plurality of shafts by the predetermined angle with reference to the axis of each shaft and then grinding the respective shafts using the wheel.

The wheel may include a grinding surface convexly curved with reference to an axis that is perpendicular to a rotation axis of the wheel.

The rotation axis of the wheel may be parallel with the axis of each of the plurality of shafts.

The forming the first cutting surface, the forming the second cutting surface, the forming the third cutting surface, and the forming the fourth cutting surface may include rotating the shaft in one of the clockwise and counterclockwise directions.

The predetermined angle may be greater than 90° and smaller than 180°.

According to the exemplary embodiments of the present invention, a trocar having maximized penetration force, a method for manufacturing the trocar that can improve productivity and work convenience, and a method for continuously manufacturing the trocar can be implemented. However, the scope of the present invention is not limited by such effects.

DETAILED DESCRIPTION OF THE EMBODIMENTS

Exemplary embodiments of the present invention will be hereinafter described in detail with reference to the accompanying drawings. The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. In addition, for better comprehension and ease of description, the size of each of constituent elements may be exaggerated or minimized.

In the following exemplary embodiments, x, y, and z axes are not limited to three axes on the orthogonal coordinate system, and may have a broader meaning including the three axes. For example, the x axis, the y axis, and the z axis may be perpendicular to each other, but may indicate directions that are different from each other. Further, in the following exemplary embodiments, the term "concave" includes "partially concave".

A trocar according to an exemplary embodiment of the present invention includes a sharp end, a cutting edge, and a cutting surface. More specifically, the trocar includes a sharp end, at least three concave cutting edges extended from the sharp end, and at least three concave cutting surfaces forming the at least three cutting edges. Such a trocar is manufacturing by processing an end of a long shaft. For example, as shown in the accompanying drawings, the trocar is manufactured by processing one end of a cylindrical-shaped long shaft. However, this is not restrictive, and the trocar can be manufactured by processing a shaft having various shapes. Meanwhile, a groove (not shown) is formed in the middle of the shaft to collect subcutaneous tissue.

Hereinafter, respective exemplary embodiments of the present invention will be described with reference to the accompanying drawings.

Figure 1:
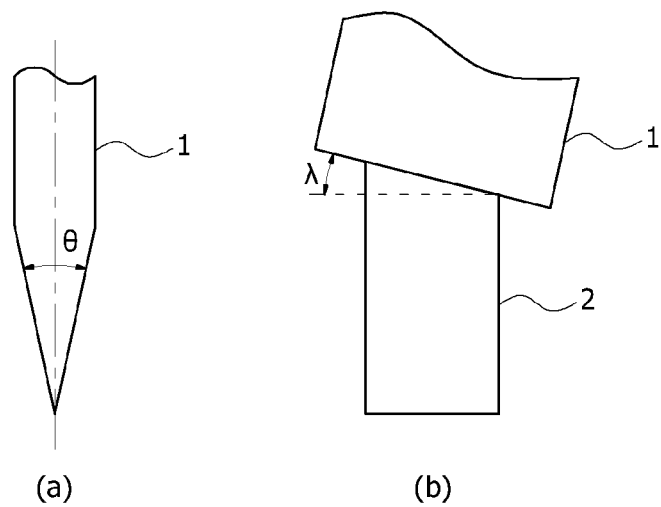
FIG. 1 is a top plan view schematically illustrating a trocar.
Figure 2:
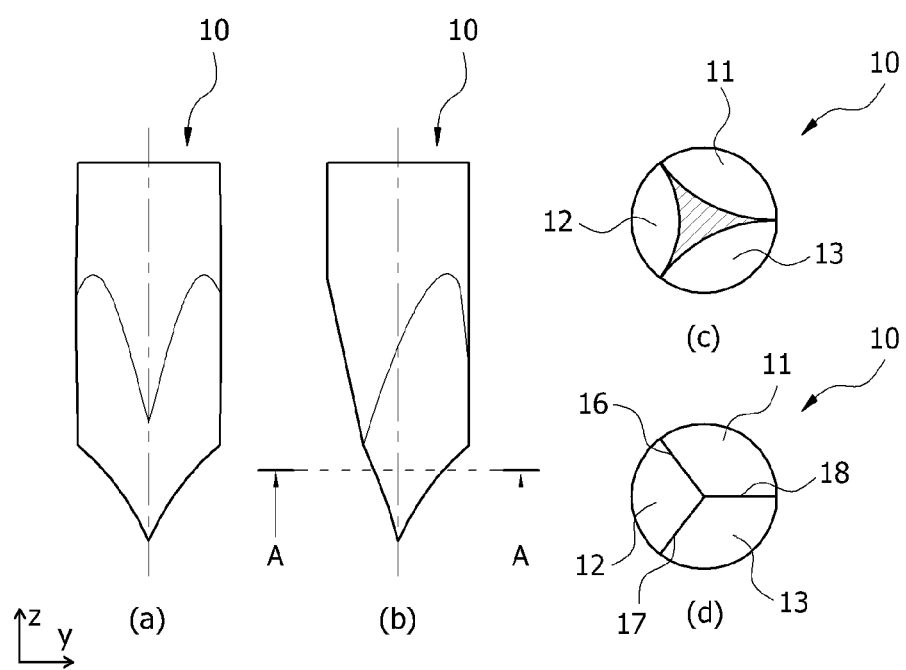
FIG. 2 schematically illustrates a trocar according to an exemplary embodiment of the present invention.

FIG. 2 schematically illustrates a trocar 10 according to an exemplary embodiment of the present invention, wherein (a) is a front view, (b) is a side view, (c) is a cross-sectional view of (b) taken along the line A-A, and (d) is a bottom view of (b). The trocar 10 according to the present exemplary embodiment includes a sharp end, three concave cutting edges 16, 17, and 18, and three cutting surfaces 11, 12, and 13.

The cutting surfaces 11, 12, and 13 are concave and are continuously connected with each other. The cutting edges 16, 17, and 18 are formed by continuously connecting the three cutting surfaces 11, 12, and 13. The sharp end is formed by the three cutting edges 16, 17, and 18 and the three cutting surfaces 11, 12, and 13.

The trocar 10 having the three cutting surfaces 11, 12, and 13 and the three cutting edges 16, 17, and 18 may be manufactured by grinding a shaft using a wheel. In this case, the shaft may have a shape of a cylindrical bar. Specifically, the cutting surfaces 11, 12, and 13 are continuously ground using one wheel such that the trocar 10 can be manufactured.

Figure 3:
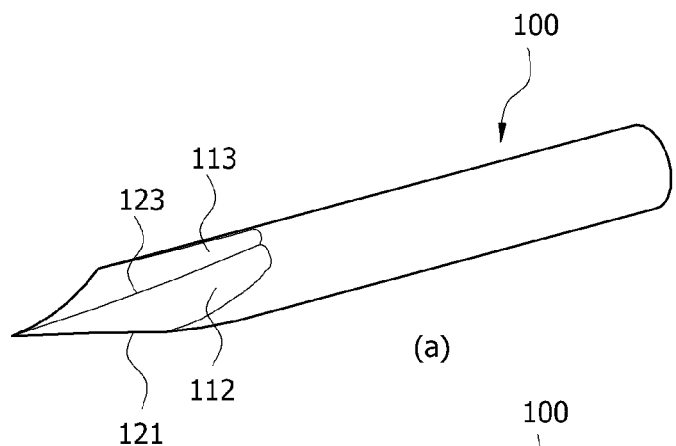
FIG. 3 schematically illustrates a trocar according to another exemplary embodiment of the present invention.
Figure 3:
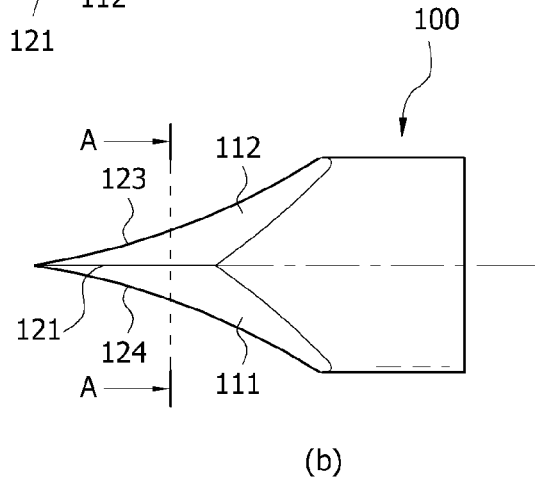
Figure 3:
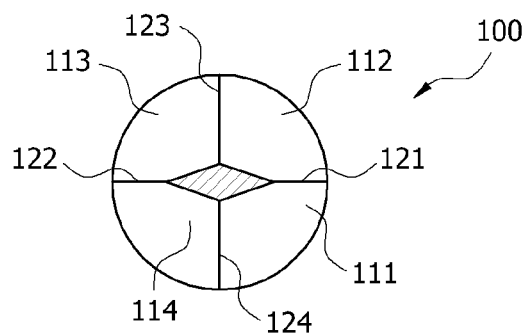

FIG. 3 schematically illustrates a trocar 100 according to another exemplary embodiment of the present invention, wherein (a) is a perspective view, (b) is a side view, and (c) is a cross-sectional view of (b) taken along the line A-A. The trocar 100 according to the present exemplary embodiment includes a sharp end, four cutting edges, and four cutting surfaces.

The four cutting edges are disposed to diagonally spread with reference to the sharp end. Specifically, a first cutting edge 121 and a second cutting edge 122 are disposed opposite to and facing each other. The first cutting edge 121 and the second cutting edge 122 substantially have the same length.

In addition, a third cutting edge 123 and a fourth cutting edge 124 are disposed opposite to and facing each other between the first cutting edge 121 and the second cutting edge 122. In this case, the third cutting edge 123 and the fourth cutting edge 124 are longer than the first cutting edge 121 and the second cutting edge 122.

That is, the cutting edges 121, 122, 123, and 124 are sequentially arranged in a clockwise direction or a counterclockwise direction with reference to the sharp end, and long cutting edges and short cutting edges are alternately disposed.

Four concave cutting surfaces are continuously connected as previously described, thereby forming the four cutting edges and the sharp end. Specifically, a first cutting surface 111, a second cutting surface 112, a third cutting surface 113, and a fourth cutting surface 114 are continuously disposed. The first cutting surface 111 and the second cutting surface 112 form the first cutting edge 121, and the second cutting surface 112 and the third cutting surface 113 form the third cutting edge 123. The third cutting surface 113 and the fourth cutting surface 114 form the second cutting edge 122, and the fourth cutting surface 114 and the first cutting surface 111 form the fourth cutting edge 124.

In order to more smoothly penetrate an outer skin layer of a person undergoing a surgical procedure while minimizing pain of the person, the sharp end should have a smaller inner angle and a larger inclination angle of the cutting edge with respect to the outer skin layer. According to the present exemplary embodiment, the cutting surfaces and the cutting edges are made concave to minimize the inner angle and at the same time maximize the inclination angle.

An angle formed by the first cutting edge 121, the sharp end, and the second cutting edge 122 is greater than an angle formed by the third cutting edge 123, the sharp end, and the fourth cutting edge 124. Accordingly, the length of the first cutting edge 121 and the second cutting edge 122 that cut tissue can be minimized.

Figure 4:
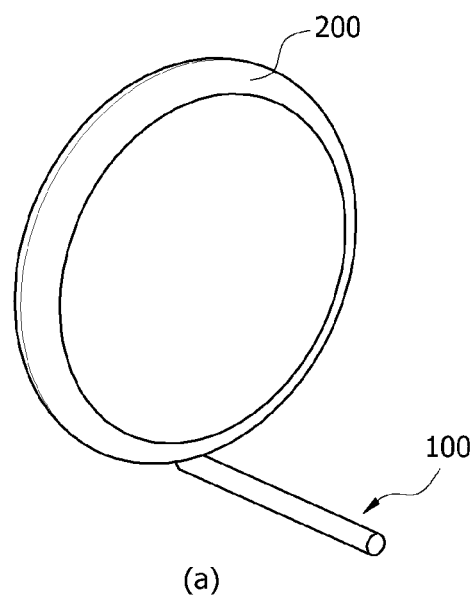
FIG. 4 illustrates a perspective view and a cross-sectional view of a manufacturing method of a trocar according to an exemplary embodiment of the present invention.
Figure 4:
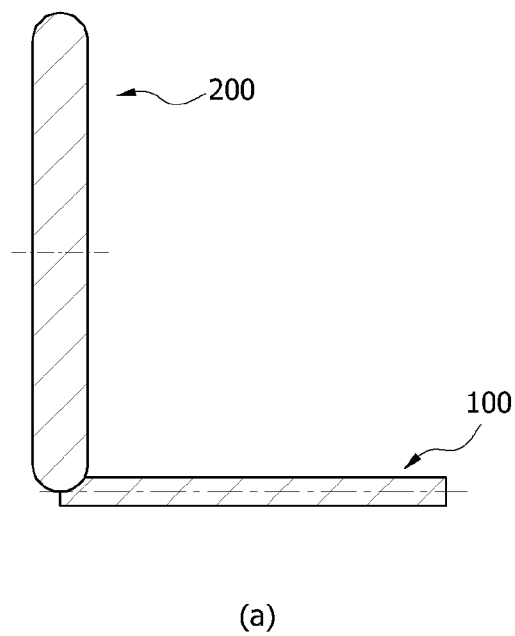

FIG. 4 illustrates a manufacturing method of a trocar 100 according to another exemplary embodiment of the present invention, wherein (a) is a perspective view and (b) is a cross-sectional view. Hereinafter, a method for manufacturing a trocar 100 will be described with reference to FIG. 4.

A trocar 100 according to the above-described exemplary embodiments can be manufactured by grinding the above-stated shaft with a wheel 200. For example, the trocar 100 can be manufactured by grinding the shaft with a cylindrical-shape wheel 200. Hereinafter, the method for manufacturing the trocar 100 will be described. The wheel 200 is provided with a grinding surface having a constant curvature in an external circumferential surface thereof.

A shaft extended in one direction is prepared, and the shaft is ground with the wheel 200 such that a concave cutting surface 11 is formed.

After forming the first cutting surface 111, the shaft is rotated by a predetermined angle with reference to the axis of the shaft and then ground such that a concave second cutting surface 112 is formed. The first cutting surface 111 and the second cutting surface 112 are connected with each other. However, this is not restrictive. The predetermined angle will be described later.

After forming the second cutting surface 112, the shaft is rotated by an angle acquired by subtracting the predetermined angle from 180° with reference to the axis of the shaft and then ground such that a concave third cutting surface 113 is formed.

Then, after forming the third cutting surface 113, the shaft is rotated by the predetermined angle with reference to the axis of the shaft and then ground such that a concave fourth cutting surface 114 is formed.

The processes for forming the first to fourth cutting surfaces 111 to 114 are performed while rotating the shaft in any one direction of the clockwise and the counterclockwise directions with reference to the axis of the shaft. That is, the plurality of cutting surfaces are sequentially and continuously formed, thereby shortening work time.

Regarding the above-stated predetermined angle, the predetermined angle is greater than 90° and smaller than 180°. Thus, the first cutting surface 111 and the second cutting surface 112 form an acute angle, and the second cutting surface 112 and the third cutting surface 113 form an obtuse angle. In addition, the third cutting surface 113 and the fourth cutting surface 114 form an acute angle, and the fourth cutting surface 114 and the first cutting surface 111 form an obtuse angle.

As previously stated, the method for manufacturing the trocar 100 is a method for grinding the shaft using one cylindrical-shaped wheel 200. However, this is not restrictive, and the shaft may be ground using a plurality of wheels 200.

Figure 5:
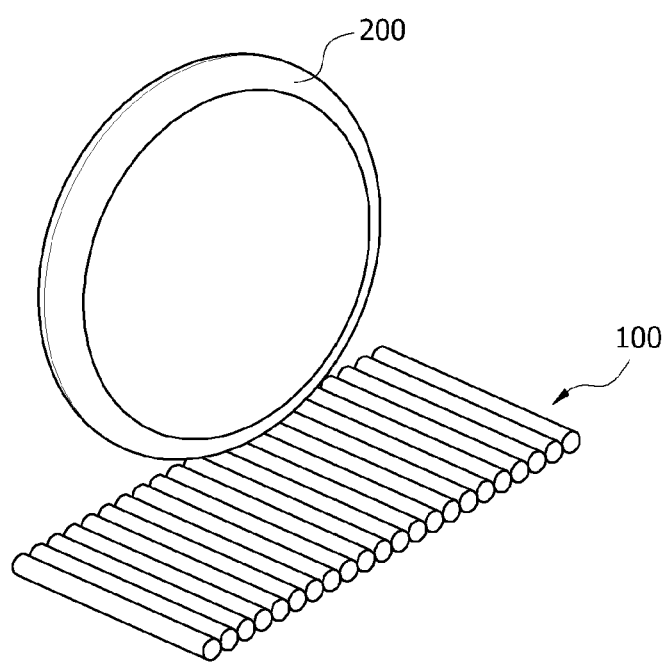
FIG. 5 is a schematic perspective view of a method for continuously manufacturing a trocar according to an exemplary embodiment of the present invention.

FIG. 5 is a schematic perspective view of a method for continuously manufacturing a trocar 100 according to another exemplary embodiment of the present invention.

A plurality of shafts are arranged in a direction that is perpendicular to an axis direction of the shaft. Here, the perpendicular direction not only includes a mathematically perpendicular range but also includes a substantially perpendicular range.

The plurality of shafts are ground using a wheel 200 to continuously form a concave first cutting surface 111 in each of the plurality of shafts.

The plurality of shafts are respectively rotated by a predetermined angle with reference to an axis of each shaft, and the plurality of shafts are ground using the wheel 200 such that a concave second cutting surface 112 is continuously formed in each of the plurality of shafts.

The plurality of shafts are rotated by an angle acquired by subtracting a predetermined angle from 180° with reference to the axis of each shaft, and then the plurality of shafts are ground using the wheel 200 such that a concave third cutting surface 113 is continuously formed in each of the plurality of shafts.

In addition, the plurality of shafts are respectively rotated by a predetermined angle with reference to an axis of each shaft, and then the plurality of shafts are ground with the wheel 200 such that a concave fourth cutting surface 114 is formed in each of the plurality of shafts.

The wheel 200 includes a convexly curved grinding surface. Specifically, an external circumferential surface of the wheel 200 is convex with a constant curvature with reference to an axis that is substantially perpendicular to a rotation axis of the wheel 200. In addition, the rotation axis of the wheel 200 is disposed in parallel with the axis of the plurality of shafts. Accordingly, the shafts may be continuously processed by moving the wheel 200 or the plurality of shafts. In this case, a movement direction of the wheel 200 or the plurality of shafts is substantially perpendicular to the axis of each shaft. The wheel 200 and the plurality of shafts may be moved in the opposite direction to process the shafts.

The processes for forming the first to fourth cutting surfaces 111 to 114 are performed while rotating the shaft in any one direction of the clockwise and the counterclockwise directions with reference to the axis of the shaft. That is, the plurality of cutting surfaces are sequentially and continuously formed, thereby shortening work time.

Regarding the above-stated predetermined angle, the predetermined angle is greater than 90° and smaller than 180°. Thus, the first cutting surface 111 and the second cutting surface 112 form an acute angle, and the second cutting surface 112 and the third cutting surface 113 form an obtuse angle. In addition, the third cutting surface 113 and the fourth cutting surface 114 form an acute angle, and the fourth cutting surface 114 and the first cutting surface 111 form an obtuse angle.

As previously stated, the method for manufacturing the trocar 100 is a method for grinding the shaft using one cylindrical-shaped wheel 200. However, this is not restrictive, and the shaft may be ground using a plurality of wheels 200.

As described, the trocar 100 can be continuously manufactured and thus the trocar 100 can be mass produced, thereby maximizing productivity.

The accompanying drawings and the detailed description of the invention are only illustrative and are used for the purpose of describing the present invention, but those skilled in the art will understand that various modifications and other equivalent embodiments of the present invention are possible. Consequently, the true technical protective scope of the present invention must be determined based on the technical spirit of the appended claims.

<Description of symbols>

| 1, 10, 100: trocar | 2: skin tissue |
| 111: first cutting surface | 112: second cutting surface |
| 113: third cutting surface | 14: fourth cutting surface |
| 121: first cutting edge | 122: second cutting edge |
| 123: third cutting edge | 124: fourth cutting edge |

What is claimed is:

1. A method for manufacturing a trocar, comprising:
   forming a concave first cutting surface by grinding a shaft extended in one direction;
   forming a concave second cutting surface by rotating the shaft by a predetermined angle with reference to an axis of the shaft and then grinding the shaft after forming the first cutting surface;
   forming a concave third cutting surface by rotating the shaft by an angle acquired by subtracting the predetermined angle from 180° with reference to the axis of the shaft and then grinding the shaft after forming the second cutting surface; and
   forming a concave fourth cutting surface by rotating the shaft by the predetermined angle with reference to the axis of the shaft and then grinding the shaft after forming the third cutting surface.

2. The method for forming the trocar of claim 1, wherein the forming the first cutting surface, the forming the second cutting surface, the forming the third cutting surface, and the forming the fourth cutting surface comprise rotating the shaft in one of clockwise and counterclockwise directions.

3. The method for forming the trocar of claim 1, wherein the predetermined angle is greater than 90° and smaller than 180°.

4. A method for continuously manufacturing a trocar, comprising:

preparing a plurality of shafts in a direction that is perpendicular to an axis direction of each shaft;

continuously forming a concave first cutting surface in each of the plurality of shafts by grinding the plurality of shafts using a wheel;

continuously forming a concave second cutting surface by rotating each of the plurality of shafts by a predetermined angle with reference to an axis of each of the plurality of shafts and grinding the respective shafts using the wheel;

continuously forming a concave third cutting surface by rotating the respective shafts by an angle acquired by subtracting the predetermined angle from 180° with reference to the axis of each shaft and grinding the respective shafts using the wheel; and continuously forming a concave fourth cutting surface by rotating the plurality of shafts by the predetermined angle with reference to the axis of each shaft and then grinding the respective shafts using the wheel.

5. The method for continuously manufacturing the trocar of claim 4, wherein the wheel comprises a grinding surface convexly curved with reference to an axis that is perpendicular to a rotation axis of the wheel.

6. The method for continuously manufacturing the trocar of claim 5, wherein the rotation axis of the wheel is parallel with the axis of each of the plurality of shafts.

7. The method for continuously manufacturing the trocar of claim 4, wherein the forming the first cutting surface, the forming the second cutting surface, the forming the third cutting surface, and the forming the fourth cutting surface comprise rotating the shaft in one of the clockwise and counterclockwise directions.

8. The method for continuously manufacturing the trocar of claim 4, wherein the predetermined angle is greater than 90° and smaller than 180°.

* * * * *